United States Patent
Zou

(10) Patent No.: US 9,657,086 B2
(45) Date of Patent: May 23, 2017

(54) WHOLE EGG PROTEIN PEPTIDES, PREPARATION METHOD AND USE THEREOF

(75) Inventor: Yuandong Zou, Hubei (CN)

(73) Assignee: WUHAN JIUSHENGTANG BIOENGINEERING CO., LTD, Hubei (CN)

( * ) Notice: Subject to any disclaimer, the term of this patent is extended or adjusted under 35 U.S.C. 154(b) by 0 days.

(21) Appl. No.: 13/818,642

(22) PCT Filed: Aug. 24, 2010

(86) PCT No.: PCT/CN2010/001287
§ 371 (c)(1),
(2), (4) Date: May 3, 2013

(87) PCT Pub. No.: WO2012/024817
PCT Pub. Date: Mar. 1, 2012

(65) Prior Publication Data
US 2013/0209497 A1    Aug. 15, 2013

(51) Int. Cl.
*C12P 1/00* (2006.01)
*C07K 16/02* (2006.01)
*A61K 35/57* (2015.01)
*A61K 38/01* (2006.01)
*C07K 14/465* (2006.01)
*C12P 21/06* (2006.01)

(52) U.S. Cl.
CPC .............. *C07K 16/02* (2013.01); *A61K 35/57* (2013.01); *A61K 38/012* (2013.01); *C07K 14/465* (2013.01); *C12P 21/06* (2013.01)

(58) Field of Classification Search
None
See application file for complete search history.

(56) References Cited

U.S. PATENT DOCUMENTS

| 5,731,290 A | * | 3/1998 | Schneider ............. A23L 1/3051 514/42 |
| 2008/0268095 A1 | * | 10/2008 | Herzog ............................ 426/2 |
| 2009/0075904 A1 | * | 3/2009 | Boots ................... A61K 38/018 514/1.1 |

FOREIGN PATENT DOCUMENTS

| CN | 1483830 A | | 3/2004 |
| CN | 101675938 A2 | | 3/2010 |
| CN | 101675938 A2 | * | 3/2010 |

OTHER PUBLICATIONS

Global Patent Search Network translation of CN101675938A2, accessed Nov. 15, 2013.*
http://www.food.com/recipe/pineapple-ham-and-cheese-omelet-333209, published Oct. 27, 2008, accessed Apr. 10, 2014.*
Zhou et al., Eur. Food Res. Technol. 226: 985-989 (2008).*
Kortt et al., Biochemistry 13(10): 2029-2037 (1974).*

(Continued)

*Primary Examiner* — Erin M Bowers
(74) *Attorney, Agent, or Firm* — Knobbe, Martens, Olson & Bear, LLP

(57) ABSTRACT

Provided are whole egg protein peptides and the preparation method thereof, wherein the whole egg protein peptides are obtained by adopting compound proteases composed of pawpaw protease, fig protease and pineapple protease to enzymatically hydrolyze the whole egg protein powder. The whole egg protein peptides can be used for manufacture of products for enhancing immunity.

7 Claims, 1 Drawing Sheet

(56) References Cited

OTHER PUBLICATIONS http://web.archive.org/web/20080229022846/http://en.wikipedia.org./wiki/Pectin, archived Feb. 29, 2008, accessed Apr. 10, 2014.*
Braga et al., Surgery 132(5): 805-814 (2002).*
Taylor, http://healthyeating.sfgate.com/levels-arginine-egg-contain-4066.html, accessed Aug. 21, 2015.*
Schlessingerman, http://web.archive.org/web/20070423024255/http://hypertextbook.com/facts/2003/AlexSchlessingerman.shtml, archived Apr. 23, 2007, accessed Apr. 14, 2014.*
Yapo, Biomacromolecules 10: 717-721 (2009).*
Redgwell et al., Carbohydrate Polymers 84: 1075-1083 (2011).*
Smale et al., Annu. Rev. Immunol. 20: 427-462 (2002).*
O'Garra et al., Nature Medicine 10(8): 801-805 (2004).*
International Search Report issued on May 26, 2011 for International Application No. PCT/CN2010/001287.
Mine Y. et al., "New insights in biologically active proteins and peptides derived from hen egg", World's Poultry Science Journal, Mar. 2006, vol. 62, No. 1, pp. 87-95.

* cited by examiner

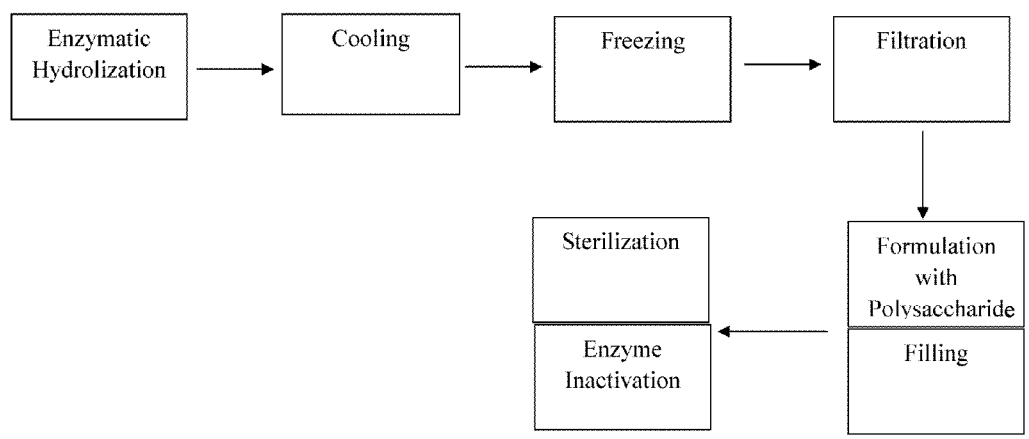

WHOLE EGG PROTEIN PEPTIDES, PREPARATION METHOD AND USE THEREOF

CROSS REFERENCE TO RELATED APPLICATIONS

This application is the U.S. National Phase of International Application No. PCT/CN2010/001287, filed Aug. 24, 2010, designating the U.S. and published as WO2012/024817 in Chinese on Mar. 1, 2012.

TECHNICAL FIELD

The present invention relates to a method for preparing a new peptide-type immunizing agent of whole egg protein peptides and use thereof.

BACKGROUND

Peptide-type immunizing agents generally belong to a class of polypeptide hormones, most of which are drugs, such as thymic peptide, thymic pentapeptide, immunoglobulin, gamma globulin, human serum albumin, interferon, tumor necrosis factor, interleukin I, interleukin II, interleukin III and the like. These peptide-type immunizing agents are all isolated and extracted from glands, tissues or blood of an animal. These polypeptide drugs are mostly an injection, and can only be applied on certain patients. During the use, a response such as rejection, allergy and side effect tends to occur. It is necessary to be cautious and under physician's strict supervision for the application.

DISCLOSURE OF THE INVENTION

The present invention aims to provide a peptide-type immunizing agent of whole egg protein peptides and a method for preparing the same.

Whole egg protein peptides provided in the invention are prepared according to following method: the whole egg protein powders is enzymically degraded using compound plant proteases to obtain said whole egg protein peptides.

In above method, said compound plant proteases may be comprised of pawpaw protease, fig protease and pineapple protease, with an enzyme activity ratio of (1-1.2 million) U:(0.3-0.4 million) U:(5.6-7 million) U.

The whole egg protein powders may be prepared from at least one of following bird eggs as raw materials: chicken, duck, goose, quail, sparrow, pigeon, turtledove and ostrich eggs.

In the enzymatic degradation reaction system, the ratio of whole egg protein powders to water by mass part is 1:8-10, the amounts of respective enzymes required for enzymically degrading per gram of whole egg protein powders are: 50-60 thousand U of pawpaw protease, 15-20 thousand U of fig protease, and 280-350 thousand U of pineapple protease. The enzymatic degradatation is performed at a temperature of 48-50° C., for a period of 3-4 hours, with a pH value of 7.5-8.5.

After the end of enzyme-catalyzed degradation reaction, it is also required to treat the enzymatic hydrolyzate with sterilization and enzyme inactivation, followed by cooling and freezing treatment, to obtain final whole egg protein peptides. The freezing is at a temperature of 4-8° C. for a period of 48 hours; and the sterilization and enzyme inactivation are performed at a temperature of 100° C. for a period of 10 minutes.

In the invention, the enzyme activity unit, U, refers to an enzyme amount required for converting 1 μmole of substrate or required for converting 1 μmole of relevant groups per minute under specific conditions (25° C., pH 7.0).

The whole egg protein peptides obtained from the invention comprise polypeptides, oligopeptides, 20 amino acids (8 of which are amino acids that are essential for human bodies and cannot be synthesized), various vitamins (VA, VC, VE, B1, B2, B6, B12), calcium, and a number of various organic natural trace elements that are extremely easy to be absorbed by human bodies (CPPS, protein zinc, selenium, magnesium, copper, iron, manganese and the like, which are naturally chelated with proteins). Each of the polypeptides and oligopeptides has a relative molecular mass below 1000 Da, and is comprised of 2-6 amino acids. The whole egg protein peptides may be present in a form of concentrated liquid, freeze-dried powders, spray-dried dry powders, an aqueous agent or a solid agent.

The invention has a further object to provide use of the whole egg protein peptides.

The use of whole egg protein peptides provided in the invention is its use in manufacture of products for enhancing immunity.

The invention has a still further aim to provide a product for enhancing immunity.

The product for enhancing immunity provided in the invention has active ingredients comprising the whole egg protein peptides provided by the invention. The product may be a drug or a healthcare product.

Of course, it is also possible to, as desired, add to the product an additional substance that is capable of enhancing immunity, such as jujube polysaccharide and lycium barbarum polysaccharide. In the product for enhancing immunity, a mass ratio of whole egg protein peptides, jujube polysaccharide and lycium barbarum (Wolfberry) polysaccharide may be (900-1200):(8-30):(3-15).

For a drug or healthcare product for enhancing immunity that is prepared with whole egg protein peptides as active ingredients, one or more pharmaceutically acceptable carriers may be further added as need. The carriers comprise conventional diluents, excipients, fillers, binders, wetting agents, disintegrants, absorption-promoting agents, surfactants, adsorption carriers, lubricants and the like in the pharmaceutical field.

The drug for enhancing immunity may be prepared in various forms such as an oral liquid, a tablet, a granulated agent, a capsule, a paste, a film agent and the like. A drug in each of above dosage forms may be prepared according to a conventional method in the pharmaceutical field, and the resultant drug has no a bitter taste.

One of significant features of the invention is that an enzymic degradation is performed on whole egg protein powders as raw materials. All of above eggs have a protein score close to 100, their proteins are close to those in human bodies and will be easily absorbed and utilized by human. The whole egg selection represents a scientific selection. If selecting only egg white proteins, proteins and many nutrients in egg yolk will be lost; if selecting only egg yolk, proteins in egg white will do so, thus selecting whole egg is namely a selection of entire nutrition system with not only a comprehensive nutrition, but also a synergistic effect that may be exerted by nutritive materials to each other.

The invention adopts a scientific formulation of compound plant proteases of three enzymes, i.e., pawpaw protease, fig protease and pineapple protease, to form a compound enzymic preparation, so as to catalyze and degrade whole egg protein powders so that whole egg protein peptides are obtained. The whole egg protein peptides can replace a polypeptide hormone-type immunizing agent and have an immunomodulatory effect as the polypeptide hormone-type immunizing agent. Polypeptide hormone-type immunizing agents are drugs that can only be applied to patients, while the product of the invention may be prepared as an oral polypeptide nutritional immunologic agent, which can have not only an therapeutic effect on a patient, but also an effect of immunity enhancement and disease prevention and fitness on a disease-free person. The product is an oral preparation, which can be carried more conveniently and administered safer than an injection, and will not cause a response such as rejection, allergy or other side effect in use, without a need of supervision from physicians during the use. It may be used for a plurality of diseases and sub-health states caused by low immune function, immune dysfunction, decreased immune function, impaired immune organs and the like, and additionally may be used for protein nutrient-deficient individuals and people having many diseases and sub-health states caused by protein nutrient deficiency, or may used for preventing a cold, and for people after exercise, delivery, disease, surgery to promote the "Negative Nitrogen Balance," and has a better effect on recovery after delivery or disease, wound healing, liver protection, sobering, restoration of appetite, promotion of sleep, recovery of renal function, stimulating phagocytosis ability of the macrophages, inhibiting growth of tumor cells, elevating leucocyte level, and the like.

DESCRIPTION FOR DRAWING

FIG. 1 is a flowchart for a manufacture process of preparing the whole egg protein peptides in the invention.

DETAILED DESCRIPTION OF CERTAIN ILLUSTRATIVE EMBODIMENTS

The experimental methods as described below, without a specific instruction, are all conventional methods; The reactants and materials, without a specific instruction, are all commercially available.

EXAMPLE 1

Preparation of an Oral Liquid of Whole Egg Protein Peptides for Enhancing Immunity Whole egg protein powders (freeze-dried dry powders or spray-dried dry powders) were placed in a fermenter, water was added with a mass equivalent to 10 times of the whole egg protein powders. When temperature was gradually rised to 50° C., compound proteases formulated according to the amount of respective enzyme required for enzymically hydrolyzing per gram of whole egg protein powders: 50 thousand U of pawpaw protease, 20 thousand U of fig protease, and 350 thousand U of pineapple protease, were added to the fermenter for enzymic hydrolyzation. Temperature was always maintained at 50° C. After enzymically hydrolyzing for 4 hours, treatments of sterilization and enzyme inactivation were conducted, followed by cooling down to 60° C. and filling in barrels. When cooled down to normal temperature, they were put into a refrigerator, and subjected to filtration after a frozen settlement for 2 days, then a concentrated liquid of whole egg protein peptides were obtained. Next, an formulation was prepared, in which the composition of effective ingredients was: 1000 mg±10% of whole egg protein peptides included in per 100 ml of an oral liquid. After preparation, it was subjected to filling and sterilized at 100° C. for 10 minutes, then an oral liquid for enhancing immunity was obtained.

EXAMPLE 2

Preparation of an Whole Egg Protein Peptide Oral Liquid Containing Jujube Polysaccharide and Lycium Barbarum Polysaccharide for Enhancing Immunity Whole egg protein powders (freeze-dried dry powders or spray-dried dry powders) were placed in a fermenter, and water was added with a mass equivalent to 8 times of the whole egg protein powders. When the temperature was gradually rised to 48° C., compound proteases that were formulated with three enzymes in accordance with that enzymic hydrolyzation of per gram of whole egg protein powders required 60 thousand U of pawpaw protease, 15 thousand U of fig protease, and 280 thousand U of pineapple protease, were added to the fermenter for enzymic hydrolyzation. Temperature was always maintained at 48° C. After enzymically hydrolyzing for 3.5 hours, treatments of sterilization and enzyme inactivation were conducted, followed by cooling down to 60° C. and filling in barrels. When cooled down to normal temperature, they were put into a refrigerator, and subjected to filtration after a frozen settlement for 2 days, then a concentrated liquid of whole egg protein peptides was obtained. Next, an formulation was prepared, in which the composition of effective ingredients was: 1000 mg±10% of whole egg protein peptides, 10 mg of jujube polysaccharide, and 5 mg of lycium barbarum polysaccharide, included in per 100 ml of an oral liquid. After preparation, it was subjected to filling and sterilized at 100° C. for 10 minutes, then an oral liquid for enhancing immunity was obtained.

EXAMPLE 3

Preparation of an Whole Egg Protein Peptide Oral Liquid Containing Jujube Polysaccharide and Lycium Barbarum Polysaccharide for Enhancing Immunity Whole egg protein powders (freeze-dried dry powders or spray-dried dry powders) were placed in a fermenter, and water was added with a mass equivalent to 8 times of the whole egg protein powders. When temperature was gradually rised to 50° C., compound proteases that were formulated with three enzymes in accordance with that enzymic hydrolyzation of per gram of whole egg protein powders required 60 thousand U of pawpaw protease, 20 thousand U of fig protease and 320 thousand U of pineapple protease, were added to the fermenter for enzymic hydrolyzation. The temperature was always maintained at 50° C. After enzymically hydrolyzing for 3 hours, they were subjected to cooling and filling in barrels. When further cooled down to 12° C., they were put into a refrigerator, and subjected to filtration after a frozen settlement for 2 days, then a concentrated liquid of whole egg protein peptides was obtained. Next, an formulation was prepared, in which the composition of effective ingredients was: 1000 mg±10% of whole egg protein peptides, 15 mg of jujube polysaccharide and 10 mg of lycium barbarum polysaccharide, included in per 100 ml of an oral liquid. After preparation, it was subjected to filling and sterilized at 100° C. for 10 minutes, then an oral liquid for enhancing immunity was obtained.

EXAMPLE 4

Preliminary Stability Test on the Oral Liquid for Enhancing Immunity

Test sample: the oral liquid prepared in Example 1
Examination Indexes:
1. Characters: the shape (comprising color) and smell of a sample was examined according to a conventional method.
2. Content measurement:
the content of main ingredients of a sample, i.e., peptides and amino acids, expressed in level of organic nitrogen (%), was measured with a measurement method in reference to GB5009.

3. Hygienic and physicochemical indicator examination: total number of bacteria, coliform groups, pathogens, fungi and yeast, and arsenic, lead, mercury contents of a product were examined according to the requirements of Food Hygiene GB4789, GB5009.
4. Accelerated test:
Three batches of samples (having respective batch Nos. 090718, 090720 and 090724, and all bottled) produced on different date were placed in a drier with a relative humidity of 75% (the drier had a saturated solution of sodium chloride at bottom therein). The drier was then put into an incubator at 37° C. for continuous heating for 3 months. Sampling was conducted periodically (Month 0, 1, 2, 3), and relative indicators were measured (results as shown in Tables 1-3). During the accelerated test for 3 months, none of the indicators presented a significant change. It can be calculated from this that: the products had a sample retention period of more than 2 years.

TABLE 1

Stability Results of the Sample of Batch No. 090718

| | Item | Month 0 | Month 1 | Month 2 | Month 3 |
| --- | --- | --- | --- | --- | --- |
| | | | Result | | |
| | Characters | Pale yellow liquid | Same as left | Same as left | Same as left |
| Quality indicators | pH value | 5.28 | 5.27 | 5.29 | 5.27 |
| | Peptides and amino acids (expressed in % organic nitrogen) | 0.218 | 0.216 | 0.216 | 0.213 |
| | Arsenic (mg/kg) | <0.1 | Unmeasured | Unmeasured | <0.1 |
| | Lead (mg/kg) | <0.3 | Unmeasured | Unmeasured | <0.3 |
| | Mercury (mg/kg) | Non-detected | Unmeasured | Unmeasured | Non-detected |
| Hygienic examination | Total number of bacteria (CFU/ml) | <10 | <10 | <10 | <10 |
| | Coliform groups MNP(100 ml) | <3 | <3 | <3 | <3 |
| | Fungi (CFU/ml) | Non-detected | Same as left | Same as left | Same as left |
| | Yeast (CFU/ml) | Non-detected | Same as left | Same as left | Same as left |
| | Pathogens | Non-detected | Same as left | Same as left | Same as left |

TABLE 2

Stability Results of the Sample of Batch No. 090720

| | Item | Month 0 | Month 1 | Month 2 | Month 3 |
| --- | --- | --- | --- | --- | --- |
| | | | Result | | |
| | Characters | Pale yellow liquid | Same as left | Same as left | Same as left |
| Quality indicators | pH value | 5.29 | 5.26 | 5.26 | 5.27 |
| | Peptides and amino acids (expressed in % organic nitrogen) | 0.219 | 0.216 | 0.213 | 0.218 |
| | Arsenic (mg/kg) | <0.1 | Unmeasured | Unmeasured | <0.1 |
| | Lead (mg/kg) | <0.3 | Unmeasured | Unmeasured | <0.3 |
| | Mercury (mg/kg) | Non-detected | Unmeasured | Unmeasured | Non-detected |
| Hygienic examination | Total number of bacteria (CFU/ml) | <10 | <10 | <10 | <10 |
| | Coliform groups MNP(100 ml) | <3 | <3 | <3 | <3 |

TABLE 2-continued

Stability Results of the Sample of Batch No. 090720

| Item | Month 0 | Month 1 | Month 2 | Month 3 |
|---|---|---|---|---|
| | | Result | | |
| Fungi (CFU/ml) | Non-detected | Same as left | Same as left | Same as left |
| Yeast (CFU/ml) | Non-detected | Same as left | Same as left | Same as left |
| Pathogens | Non-detected | Same as left | Same as left | Same as left |

TABLE 3

Stability Results of the Sample of Batch No. 090724

| | Item | Month 0 | Month 1 | Month 2 | Month 3 |
|---|---|---|---|---|---|
| | | | Result | | |
| Quality indicators | Characters | Pale yellow liquid | Same as left | Same as left | Same as left |
| | pH value | 5.27 | 5.27 | 5.28 | 5.27 |
| | Peptides and amino acids (expressed in % organic nitrogen) | 0.216 | 0.214 | 0.213 | 0.212 |
| | Arsenic (mg/kg) | <0.1 | Unmeasured | Unmeasured | <0.1 |
| | Lead (mg/kg) | <0.3 | Unmeasured | Unmeasured | <0.3 |
| | Mercury (mg/kg) | Non-detected | Unmeasured | Unmeasured | Non-detected |
| Hygienic examination | Total number of bacteria (CFU/ml) | <10 | <10 | <10 | <10 |
| | Coliform groups MNP(100 ml) | <3 | <3 | <3 | <3 |
| | Fungi (CFU/ml) | Non-detected | Same as left | Same as left | Same as left |
| | Yeast (CFU/ml) | Non-detected | Same as left | Same as left | Same as left |
| | Pathogens | Non-detected | Same as left | Same as left | Same as left |

Conclusion: The products were stable to heat, and could be preserved at a normal temperature for 2 years.

EXAMPLE 5

Safety Evaluation Test on an Oral Liquid for Enhancing Immunity

1) Acute Toxicity Test

Animals: Kunming mice species of 18-20 g, half male and half female, 20 in total; the animals were provided by the Medically Experimental Animal Center of Hubei.

Tested drug: the oral liquid for enhancing immunity as prepared in Example 1.

Administration way: test animals were administered by gavage in 0.3 ml/10 g.b.w. The animals were fasted for 12 h before the gavage, and observed for one week.

Results: the mice presented no toxic symptoms after the gavage, and no mice were dead in one week, LD50>30 ml/kg. According to acute toxicity grading, the tested product belonged to non-toxic substance.

2) Micronucleus Test

Animals: Kunming mice species, 25-27 g.

Test method: tested drug was given with gavage twice; the animals were sacrificed 6 h after the second gavage, and taken for chest bone marrow, which was diluted with fetal calf serum for smear, and then subjected to Gimsa staining. Each of animals had 1000 polychromatic erythrocytes observed under a microscope. The number of micronucleus cell formed was recorded in permillage. The results are seen in Table 4, wherein, the CP group is a cyclophosphamide positive control group.

TABLE 4

| Test substance | Dosage (ml/mg) | Animals Number | Observed cell number | Number of micronucleus cell occurence | Micronucleus formation rate (%) |
|---|---|---|---|---|---|
| Negative control group | 0 | 10 | 10 × 1000 | 21 | 2.1 |
| Test group | 2 | 10 | 10 × 1000 | 29 | 2.9 |
|  | 4 | 10 | 10 × 1000 | 27 | 2.7 |
|  | 6 | 10 | 10 × 1000 | 21 | 2.1 |
|  | 8 | 10 | 10 × 1000 | 26 | 2.6 |
|  | 10 | 10 | 10 × 1000 | 24 | 2.4 |
| CP group (mg/kg) | 60 | 8 | 8 × 1000 | 325 | 40.6 |

Conclusion: none of the test groups presented a significant difference as compared with the results of the negative control group, suggesting that the bone marrow micronucleus test had a negative result on the test product.

3) Mouse Sperm Abnormality Test:

Animals: Kunming mice species, 23-25 g.

Test method: after continuous gavage for 5 days, the mice were fed for further 30 days. The animals were sacrificed, and taken epididymis of both sides for smear. Each of animals was counted for 1000 sperms with a complete structure, and calculated for sperm abnormality incidence. The results are shown in Table 5, wherein the CP group is a cyclophosphamide positive control group.

TABLE 5

| Test substance | Dosage (ml/mg) | Animals Number | Observed cell number | Number of micronucleus cell occurence | Micronucleus formation rate (%) |
|---|---|---|---|---|---|
| Negative control group | 0 | 5 | 5 × 1000 | 89 | 1.78 |
| Test groups | 5 | 5 | 5 × 1000 | 91 | 1.82 |
|  | 10 | 5 | 5 × 1000 | 99 | 1.98 |
|  | 15 | 5 | 5 × 1000 | 97 | 1.94 |
| CP group (mg/kg) | 30 | 5 | 5 × 1000 | 359 | 7.18 |

Conclusion: none of the test groups presented a significant difference as compared with the results of the negative control group; suggesting that the sperm abnormality test had a negative result on the test product.

4) Ames Test

A test was performed with four strains of histidine defective *Salmonella Typhimurium*, TA97, TA98, TA100 and TA102, which had been identified for satisfying biological requirements, respectively: a polychlorinated biphenyl (PCB) induced rat liver homogenate was used as an activation system in vitro ($+S_9$). Test products were divided into three dose groups, with samples being diluted at different concentrations, where after sterilization 0.5 ml of the samples was added per dish, to have a concentration of 1:10, 1:100, 1:1000, respectively. Results were recorded for two repeated parallel samples using an incorporation method. The results are shown in Table 6.

TABLE 6

| Test substance | Concentration (dilution factor) | Number of revertant colonies | | | | | | | |
|---|---|---|---|---|---|---|---|---|---|
|  |  | $-S_9$ | | | | $+S_9$ | | | |
|  |  | TA97 | TA98 | TA100 | TA102 | TA97 | TA98 | TA100 | TA102 |
| Spontaneous revertant | 0 | 118 | 26 | 139 | 249 | 152 | 24 | 147 | 238 |
| Test product | 1:1000 | 156 | 21 | 169 | 205 | 163 | 29 | 154 | 205 |
|  | 1:100 | 143 | 29 | 183 | 186 | 175 | 31 | 132 | 218 |
|  | 1:10 | 132 | 38 | 179 | 298 | 146 | 35 | 168 | 236 |
| Positive control | 0.0003 | >5000 | >3000 | 396 | 25 | 164 | >3000 | >3000 | 283 |

Note:

$-S_9$ positive control group is 3-nitro9-fluorenone (2.4.7-TNFone), and $+S_9$ positive control groups is 2-aminofluorene (2-AF).

It can be known from above table that none of the test groups had a number of revertant colonies more than 2 times of that of spontaneous revertant; and no dose-response relationship occurred, so the test result represented negative.

EXAMPLE 6

Examination of an Immunomodulatory Effect of Whole Egg Protein Peptide

1. Test animals: Kunming mice species 18-22 g, half male and half female. (provided by the Medically Experimental Animal Center of Hubei)

2. Grouping: dose grouping was that: a control group was intragastrically administered with distilled water; "The oral liquid as prepared in Example 1" had a concentration of 1% (i.e., 1000 mg/100 ml), and low-, medium-, and high-dose groups were intragastrically administered with 100 mg/kg.b.w; 300 mg/kg.b.w; and 900 mg/kg.b.w of the oral liquid, respectively; which were equivalent to 6, 18, 54 fold of a recommended intake for human, respectively. The intragastric administration lasted for one month, and then individual experiments were conducted.

3. Experimental methods and results:

3.1 ConA induced mouse spleen lymphocyte transformation test

Method: an average of pore absorbance differences for each group with or without ConA with a MTT method (ConA induced mouse spleen lymphocyte transformation test) was subjected to one-way ANOVA.

Results: as seen in Table 7.

It can be seen from Table 7 that there were significant differences between groups, and the low-dose group of the "oral liquid" presented a significantly enhanced ConA induced spleen lymphocyte proliferation ability.

TABLE 7

Effect of the "oral liquid" on Immune Function of Mouse Cell

| Group | ConA induced spleen lymphocytes proliferation N = 10 (OD difference, M ± SD) | DNFB induced DTH N = 9 (weight difference between left and right ear, mg) |
|---|---|---|
| Control group | 0.229 ± 0.075 | 16.14 ± 12.02 |
| Low dose group | 0.344 ± 0.055* | 26.89 ± 6.64* |
| Medium dose group | 0.241 ± 0.013 | 18.21 ± 6.96 |
| High dose group | 0.24. ± 0.097 | 18.89 ± 7.26 |

*$P < 0.05$ as compared with Control group.
Note:
0.2 ml was taken for $OD_{570}$ value.

3.2 Dinitrofluorobenzene (DNFB) induced delayed type hypersensitivity (DTH)

Method: ear-swelling method. After mices were sensitized with DNFB, the right ear was challenged with DNFB again on day 5, and then the animals were sacrificed after 24 h, and cut for left and right auricular conchas, from which a piece of ear of a diameter of 8 mm was removed using a puncher, and weighted; the level of DTH was represented by a weight difference between left and right ears.

Results: as seen in Table 7.

It can be seen from Table 7 that: the low-dose group of the "oral liquid" allowed a significant improvement of response in mice to DNFB induced DTH.

3.3 Examination of serum hemolysin: a hemagglutination method. Antibody-integrals were calculated based on the level of serum cohesion level, and an average of each of groups of the antibody-integrals was subjected to one-way ANOVA.

Results: as seen in Table 8.

It can be seen from Table 8 that there were significant differences between groups, Low-, and high-dose groups of the "oral liquid" allowed a significantly increased content of serum hemolysin.

TABLE 8

Effect of the "Oral Liquid" on Humoral Immune Function of Mice

| Group | N | Serum hemolysin (antibody-integral) |
|---|---|---|
| Control group | 10 | 66.7 ± 11.6 |
| Low dose group | 10 | 90.4 ± 8.40* |
| Medium dose group | 10 | 73.5 ± 17.7 |
| High dose group | 10 | 80.9 ± 5.09* |

*$P < 0.01$ as compared with the control group.

3.4 Experiment of Intraperitoneal Macrophage's phagocytosis of chicken erythrocytes Method: a semi-in vivo method. A suspension of 20% chicken erythrocytes was prepared; 1 mL of which was intraperitoneally injected into each of mices; after 30 min the animals were sacrificed, opened at abdomen, and intraperitoneally injected 2 mL of normal saline, which were then averaged to drip on 2 sheets of slides, and incubated at 37° C. for 30 min; thereafter, the slides were rinsed with normal saline, air-dried, fixed with acetone-methanol solution of 1:1, stained with 4% Giemsa-phosphate buffer for 3 min, and further rinsed with distilled water and air-dried. 100 macrophages were counted under an oil immersion lens, and the phagocytic rate and phagocytic index were calculated according to the equation below:

$$\text{Phagocytic rate (\%)} = \frac{\text{Number of macrophages that phagocytose chicken erythrocytes}}{\text{Number of macrophages counted}} \times 100$$

$$\text{Phagocytic index} = \frac{\text{Number of chicken erythrocytes that were phagocytosed}}{\text{Number of macrophages counted}}$$

Results: as seen in Table 9. It can be seen from Table 9 that the low- and high-dose group of the "oral liquid" had phagocytic rates significantly higher than that of the control group; and the low-dose group had a phagocytic index significantly higher than that of the control group.

TABLE 9

Effect of the "oral liquid" on the phagocytic function of macrophages in peritoneal cavity of mice

| Group | N | Phagocytic rate (%) | Phagocytic index |
|---|---|---|---|
| Control group | 10 | 77.2 ± 2.15 | 1.037 ± 0.053 |
| Low dose group | 10 | 81.5 ± 2.76** | 1.237 ± 0.145 |
| Medium dose group | 10 | 79.3 ± 3.95 | 1.097 ± 0.130 |
| High dose group | 10 | 80.2 ± 3.52 | 1.106 ± 0.095 |

*$P < 0.05$ as compared with the control group, and
**$P < 0.01$ as compared with the control group.

3.5 Mice carbon clearance test

Method: a method specified according to a procedure. A swallowing index was calculated for mices of each of groups based on the carbon concentrations in blood 2 min, 10 min after injection of an ink (measured as absorbance values).

Results: as seen in Table 10. It can be seen from Table 10 that the low-dose group of the "oral liquid" allowed a significantly enhanced swallowing index of carbon clearance in mice.

TABLE 10

Effect of the "oral liquid" on mice carbon clearance function

| Group | N | Swallowing index |
|---|---|---|
| Control group | 5 | 6.609 ± 0.755 |
| Low dose group | 10 | 7.196 ± 0.489* |
| Medium dose group | 10 | 5.966 ± 0.670 |
| High dose group | 10 | 6.152 ± 0.854 |

*$P < 0.05$ as compard with the control group.

The experimental results of immunomodulatory effect showed that: "an oral liquid of whole egg protein peptides" allowed 1) an enhanced ConA induced murine spleen lymphocyte proliferation ability; 2) an enhanced dinitrofluorobenzene induced murine delayed type hypersensitivity; 3) an improved content of murine serum hemolysin; 4) an enhanced function of macrophages in murine peritoneal cavity to phagocytose chicken erythrocytes and enhanced ability of carbon clearance. According to the method of evaluating an immunomodulatory effect as specified in Item 3.1 of the Assessment Procedure and Test Methods of Healthcare Food Function, it can be considered as that the whole egg protein peptides as prepared in the invention have an immunomodulatory effect.

INDUSTRIAL APPLICATION

The present invention uses a compound enzymic preparation formed of compound plant proteases of a formulation of three enzymes: namely pawpaw protease, fig protease and pineapple protease, with whole egg protein powders as a substrate to catalyze and degrade the whole egg protein powders, so as to obtain whole egg protein peptides. The product has relatively high biological activities, and is a new immunomodulator and immunostimulant. The whole egg protein peptides of the invention can be used to develop an immune drug, healthcare food, functional food, anti-aging and infant food and nutritional supplement for seriously ill-patients. Lyophilized powders of the invention prepared by freeze-drying can be further made into a capsule or tablet, and can be deeply developed into an auxiliary therapeutic agent for tumors (enhancing immune function, increasing radiation resistance of a patient treated with radiotherapy or chemotherapy, elevating levels of red, white blood cells), an anti-inflammatory agent and an agent for the treatment of hepatitis, or an agent for preventing atypical pneumonia, and also can serve as a raw material of other drugs or as food additive. No matter the type of drug, healthcare product or functional food, the development thereof will generate great economic and social benefits, and have a very wide prospect.

What is claimed:

1. A method of enhancing immunity in a subject, the method comprising:
    preparing a composition comprising all peptides from a whole egg by a method comprising:
        enzymatically degrading peptide powders from the whole egg using a compound plant protease consisting of papain, fig protease and pineapple protease at a temperature of 48-50° C. for 3-4 hours at a pH of 7.5-8.5 so as to provide all of said enzymatically degraded peptides from a whole egg,
        wherein the amounts of respective enzymes required for enzymatically degrading per gram of the protein powder from a whole egg are: 50-60 thousand U of pawpaw protease, 15-20 thousand U of fig protease, and 280-350 thousand U of pineapple protease;
    administering by mouth the composition comprising all of said peptides obtained by enzymatically degrading all proteins from a whole egg by papain, fig protease and pineapple protease, and one or more added pharmaceutically acceptable carriers to the subject, all of said enzymatically degraded peptides from the whole egg comprising a molecular mass below 1000 Da and having 2-6 amino acids; and
    comparing an immunomodulatory effect of the composition in the subject to a control, said control not being administered with the composition, wherein the subject has enhancement on an immunological function as compared to an immunological function of the control.

2. The method according to claim 1, wherein the composition is administered orally.

3. The method according to claim 2, wherein the composition is an oral liquid.

4. The method according to claim 1, wherein the composition further comprises jujube polysaccharide and lycium barbarum polysaccharide.

5. The method according to claim 4, wherein, in the composition, the peptide, the jujube polysaccharide and the lycium barbarum polysaccharide have a mass ratio of (900-1200):(80-140):(40-70).

6. The method according to claim 1, wherein the one or more added pharmaceutically acceptable carrier is selected from the group consisting of a diluent, an excipient, a filler, a binder, a wetting agent, a disintegrant, an absorption-promoting agent, a surfactant, an adsorption carrier, and a lubricant.

7. The method according to claim 1, wherein a dose of administration ranges from 100 mg to 900 mg of the composition per kg of the subject's weight.

* * * * *

UNITED STATES PATENT AND TRADEMARK OFFICE
CERTIFICATE OF CORRECTION

PATENT NO. : 9,657,086 B2
APPLICATION NO. : 13/818642
DATED : May 23, 2017
INVENTOR(S) : Yuandong Zou et al.

Page 1 of 1

It is certified that error appears in the above-identified patent and that said Letters Patent is hereby corrected as shown below:

In the Specification

In Column 3 at Line 39, Change "methods;" to --methods.--.

In Column 4 at Line 30 (approx.), Change "Next,an" to --Next, an--.

In Column 8 at Line 61 (approx.), Change "Gimsa" to --Giemsa--.

In Column 13 at Line 16 (approx.), Change "compard" to --compared--.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*